US007927888B2

(12) United States Patent
Buckley et al.

(10) Patent No.: US 7,927,888 B2
(45) Date of Patent: Apr. 19, 2011

(54) METHOD TO FABRICATE A CHIP FOR THE DETECTION OF BIOLOGICAL ELEMENTS

(75) Inventors: Julien Buckley, Grenoble (FR); Olivier Billoint, Grenoble (FR); Guillaume Delapierre, Vif (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 12/620,881

(22) Filed: Nov. 18, 2009

(65) Prior Publication Data

US 2010/0124791 A1 May 20, 2010

(30) Foreign Application Priority Data

Nov. 20, 2008 (FR) ..................... 08 57893

(51) Int. Cl.
*H01L 21/336* (2006.01)
(52) U.S. Cl. ........ 438/1; 257/E21.409; 438/49; 438/142
(58) Field of Classification Search ...... 438/1, 141–151, 438/49, 50
See application file for complete search history.

(56) References Cited

U.S. PATENT DOCUMENTS
2008/0108164 A1   5/2008   Oleynik

FOREIGN PATENT DOCUMENTS
| DE | 44 30 811 C1 | 9/1995 |
| DE | 102 55 755 A1 | 7/2004 |
| EP | 1 557 884 A2 | 7/2005 |

OTHER PUBLICATIONS

Andreas Hierlemann, et al., "Microfabrication Techniques for Chemical/Biosensors", Proceedings of the IEEE, vol. 91, No. 6, Jun. 1, 2003, XP-011097409, pp. 839-863.
Fernando Patolsky, et al., "Fabrication of silicon nanowire devices for ultrasensitive, label-free, real-time detection of biological and chemical species", Nature Protocols, vol. 1, No. 4, 2006, pp. 1711-1724.
Yuri L. Bunimovich, et al., "Quantitative Real-Time Measurements of DNA Hybridization with Alkylated Nonoxidized Silicon Nanowires in Electrolyte Solution", Journal of American Chemical Society, 128, 2006, pp. 16323-16331.
Eric Stern, et al., "Label-free immunodetection with CMOS-compatible semiconducting nanowires", Nature, vol. 445, Feb. 2007, pp. 519-522.

*Primary Examiner* — Savitri Mulpuri
(74) *Attorney, Agent, or Firm* — Oblon, Spivak, McClelland, Maier & Neustadt, L.L.P.

(57) ABSTRACT

Improved method to fabricate a microelectronic device provided with at least one circuit to detect biological elements, comprising the steps of:
  a) forming transistors,
    depositing at least one layer in at least one insulating material (141) coating said transistors,
    forming one or more holes (143) in said layer of insulating material (141), so as to expose the upper face of the respective gate (135) of first-type transistors,
    filling the holes with a gate material,
  b) removing, at least in part, the respective gate (135) of the first-type transistors, whilst the gate of second-type transistors is protected, the method prior to or at the same time as said removal conducted at step b) further comprising the removal of said gate material.

8 Claims, 9 Drawing Sheets

METHOD TO FABRICATE A CHIP FOR THE DETECTION OF BIOLOGICAL ELEMENTS

TECHNICAL AREA

The invention relates to the field of microelectronics and more particularly to the field of microelectronic devices comprising at least one circuit for the detection of biological elements.

The invention provides for and allows the co-integration, on one same substrate, of transistors dedicated to detecting biological elements such as biological markers, together with conventional transistors provided with a gate.

It notably concerns a method to fabricate at least one microelectronic device comprising, on one same substrate, at least one circuit to detect biological elements and one or more other circuits for processing measurements.

The invention also concerns the fabrication of an electronic chip allowing the automatic determination of a medical pre-diagnosis or medical diagnosis.

STATE OF THE PRIOR ART

The fabrication of devices to detect biological molecules on a chip is known.

Document EP 1 557 884 A2 describes a biological detection chip used to detect biological elements such as DNA, chemical materials and ions.

The chip is fabricated on a SOI substrate and comprises conventional NMOS and PMOS transistors insulated by a PN junction formed at the interface of the P- and N-doped regions of the respective types of transistors.

The electric detection sensitivity of said device is insufficient.

Said chip comprises wireless transmission means with an antenna allowing transmission of a measurement signal intended to be processed by a computer.

In document: "*Fabrication of silicon nanowire devices for ultrasensitive, label-free, realtime detection of biological and chemical species*" Patolsky, G. Zheng, C. M. Lieber, *Nature protocols*, Vol. 1, N° 4, pp. 1711-1724, 2006, a device having biological detection transistors and comprising channels in the form of SI channels of nanometric size is described.

In said device, the channels are in the form of nanowires randomly distributed on metal contacts. A method to fabricate nanowires by chemical vapour deposition is given. This method does not allow precise distribution of the channels. Also, with said method, the nanowires obtained have a length and diameter which are difficult to control, which creates dispersion between the electric characteristics of the different channels.

In the document: "*Quantitative real-time measurements of DNA hybridization with alkylated non-oxidized silicon nanowires in electrolyte solution*", Y. L. Bunimovich, Y. S. Shin, W. S. Yeo, M. Amori, G. Kwong, J. R. Heath, Journal of American Chemical Society, 128, pp. 16323-16331, a method is also described for the fabrication of semiconductor components for the detection of biological elements using semiconductor nanowires. This method called SNAP for "Superlattice Nanowire Pattern Transfer" allows ordered nanowires to be obtained.

The document: "*Label-free immunodetection with CMOS-compatible semiconducting nanowires*", E. Stem, J. F. Klemic, D. A. Routenberg, P. N. Wyrembak, D. B. Turner-Evans, A. D. Hamilton, D. A. LaVan, T. M. Fahmy, M. A. Reed, Nature, Vol. 445 describes another method to fabricate nano-channels of transistors dedicated to the detection of biological elements.

Document US 2008/0108164 A1 discloses a method to fabricate a microelectronic device provided with a detection circuit for biological elements.

The fabrication of transistors to detect said circuit is difficult to implement.

A novel method is to be found to fabricate a microelectronic device provided with transistors for the detection of biological elements.

DESCRIPTION OF THE INVENTION

The present invention concerns a method to fabricate a microelectronic device provided with at least one circuit for the detection of biological elements, comprising the steps of:

a) fabricating, on a substrate, a plurality of transistors each comprising at least one gate formed of at least one layer containing at least one gate material on at least one layer of gate dielectric, said gate resting on a channel region, b) removing, at least in part, the respective gate from one or more so-called "first-type transistors" from among said transistors, whilst the respective gate of one or more other so-called "second-type transistors" amongst said transistors, is protected, c) binding or grafting biological receptors on a surface (S) of said first-type transistors, the surface facing their channel region.

The biological receptors, also called biological probes, can for example be in the form of DNA, oligo-nucleotides, proteins, enzymes, or antibodies.

Binding or grafting can be obtained via an organic layer or using organic linkers.

The organic layer or organic linkers formed on said surface are therefore chosen in relation to the biological receptor or biological probe that is to be bonded or grafted thereupon.

For example, the following associations can be used:
a nucleophilic organic layer on which electrophilic biological receptors are bonded,
an electrophilic organic layer on which nucleophilic biological receptors are bonded.

By "transistor" is meant a semiconductor-based electronic component comprising at least one semiconductor region called "channel" region between a so-called "source" region and a so-called "drain" region, and means to control the passing of an electric current in the channel region.

For the second-type transistors, the means to control the conductivity of the channel comprise a gate, whilst for first-type transistors the means to control channel conductivity comprise biological receptors (also called probes) intended to be linked or associated with biological elements (or markers) to be detected. Depending on whether or not the biological elements (or markers) are present and depending on their quantity, the conductivity of the channel of second-type transistors is destined to vary.

The method of the invention allows the co-integration, on one same substrate, firstly of transistors having a conventional structure dedicated for example to a logic control circuit and/or to signal processing, and secondly of transistors for biological detection.

The biological receptors bonded at step c) may optionally be arranged in an encapsulating layer. This allows the stability of molecule binding to be improved, and allows use of a device with a large quantity of receptors.

The biological receptors are chosen to have an affinity with one or more biological markers to be detected, namely at least one protein or antibody, or at least one virus, or oligonucleotides or DNA.

Between step a) and step b), the method may comprise the steps of:
depositing at least one layer containing at least one insulating material coating said transistors,
forming one or more holes in said layer of insulating material, so as to expose the upper face of the respective gate of the first-type transistors,
filling the holes using a gate material, chosen so that it can be selectively etched with respect to the insulating material, this filling allowing blocks in said given material to be formed resting respectively on the upper face of the gates of the first-type transistors, the method further comprising the removal of said gate material prior to or at the same time as said removal conducted at step b).

Choosing the gate material as filler material facilitates the at least partial removal of the gates at step b), and optionally to perform this removal in a single time.

The holes may have a bottom part whose surface is greater than the surface of the upper face of the gate of the first-type transistors.

This makes it possible to form blocks in said given material whose dimensions are greater than those of the gates, and thereby to overcome any alignment difficulties when it is subsequently desired to perform at least partial removal of the gates.

After filling said holes with said given material, one or more insulating layers can be formed and one or more metal interconnection levels facing said second-type transistors; the method may then further comprise: the formation, opposite the first-type transistors, of one or more openings in said insulating layers, so as to expose the blocks in said given material, the removal of said given material and the removal of the gate material at step b) being performed through said openings.

According to one first possible implementation, the gate may be entirely removed at step b), the receptor molecules being bonded on the channel region of the first-type transistors.

According to a second possible implementation, the gate may be partly removed at step b), so as to expose the gate dielectric layer, the receptor molecules being bonded on the gate dielectric layer of the first-type transistors.

The method, after step c), may further comprise the filling of the openings with at least one liquid intended to convey biological elements or biological markers to be detected.

The invention allows the use of a microelectronic device comprising on one substrate:
at least one detection circuit to detect biological elements, comprising a plurality of transistors containing at least one semiconductor channel, and biological receptors capable of receiving one or more biological elements, bonded on a surface located opposite the channel region or on the channel region,
another plurality of transistors each comprising at least one gate formed of at least one layer in at least one gate material on at least one layer of gate dielectric layer, said gate resting on a channel region.

The biological receptors may be bonded via an organic layer or organic linkers, on the channel region or on said gate dielectric layer.

The biological receptors can also be arranged in an encapsulating layer.

The biological receptors may be designed to receive at least one biological marker such as at least one protein, or at least one virus, or they may comprise nucleotides and be designed to receive DNA.

The device, on said substrate, may further comprise:
memorization means provided to memorize data on one or more measurements performed by said detection circuit, and data on reference values or ranges of reference values,
comparison means provided to compare one or more measurements with one or more reference values or ranges of reference values.

The device may also comprise, on said substrate: means to detect a difference between measurements taken by the detection circuit and reference values.

The microelectronic device of the invention may therefore be adapted to the conducting of medical diagnoses, at least in part.

BRIEF DESCRIPTION OF THE DRAWINGS

The present invention will be better understood on reading the description of examples of embodiment given solely for indication purposes and in no way limiting, with reference to the appended figures in which.

Identical similar or equivalent parts in the different figures carry the same reference numbers, to facilitate cross-reading of the figures.

The different parts shown in the figures are not necessarily shown to uniform scale, for better legibility of the figures.

DETAILED DESCRIPTION OF PARTICULAR EMBODIMENTS

One example of the method according to the invention to fabricate a microelectronic device provided with at least one detection circuit to detect biological elements or markers, and with at least one other circuit e.g. in the form of at least one logic circuit provided for the processing of measurement signals, will now be described in connection with FIGS. 1A-1O (those parts of the device dedicated to fabrication of the detection circuit and to fabrication of the logic circuit being delimited by a broken line in these figures).

The starting material of this method may be a substrate of semiconductor-on-insulator type (SOI) formed of a semiconductor carrier 100 e.g. in silicon coated with an insulating layer 101 in $SiO_2$ for example, itself coated with a thin semiconductor layer 102 in a semiconductor material such as Si for example.

Next, the active transistor regions 104a, 104b are formed in the thin semiconductor layer 102. This can be performed using at least one photolithography step, followed by etching. Lithography can be conducted using a UV beam for example or using an e-beam. During this photolithography, the steps of forming a resin mask, then of reducing the resin mask by trimming can be carried out.

The active regions can be formed with a critical dimension W of between 5 and 50 nanometers, for example of the order of several tens of nanometers e.g. of the order of 40 nanometers.

Some active regions 104a are intended for application of particular semiconductor components provided for the detection of biological elements such as biological markers, DNA, proteins, viruses. These particular semiconductor components will be called transistors and qualified as "first-type transistors" in the following description.

Figure 1A:
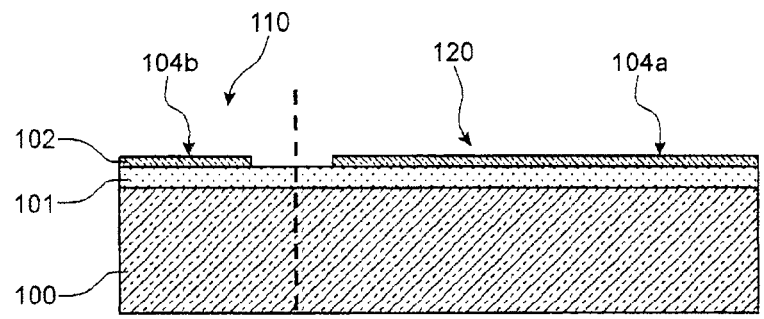
FIGS. 1A-1O illustrate one example of a method to fabricate a device according to the invention which, on one same substrate, comprises semiconductor components dedicated to the detection of biological elements, and transistors provided with a control gate of which some may be dedicated to the processing of electric signals produced by the detection transistors.

Other active regions 104b are provided for a second type of transistor, notably transistors of one or more signal processing circuits (FIG. 1A).

Figure 1B:
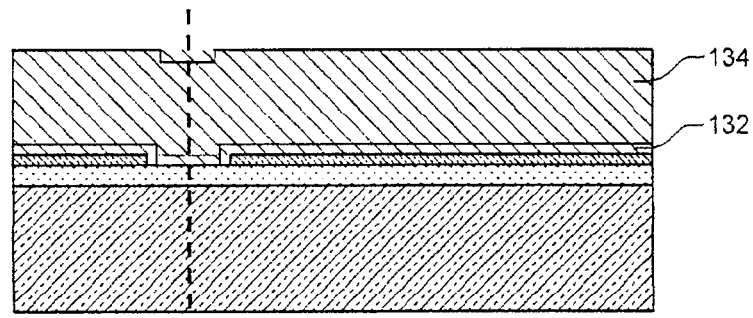

Next, a stack of gates is formed by depositing on the active regions 104a and 104b, a layer of at least one gate dielectric material 132 such as $SiO_2$, then at least one layer of gate material 134, such as polysilicon (FIG. 1B).

Figure 1C:
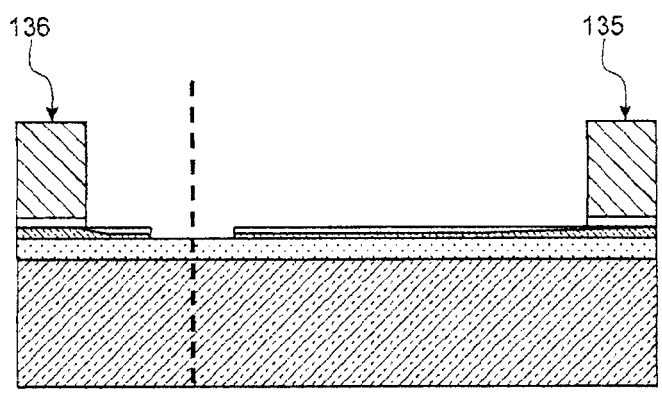

Then (FIG. 1C), patterns are made in the layer of gate material 134 and in the layer of dielectric material 132, to form patterns 135, 136 of gate electrodes for the first-type and second-type transistors respectively. These patterns may be formed using at least one photolithography step for example, followed by etching.

A step to dope source and drain regions can then be conducted, for example using at least one implanting step in some parts of the active regions 104a, 104b, located either side of the gates 135, 136.

Figure 1D:
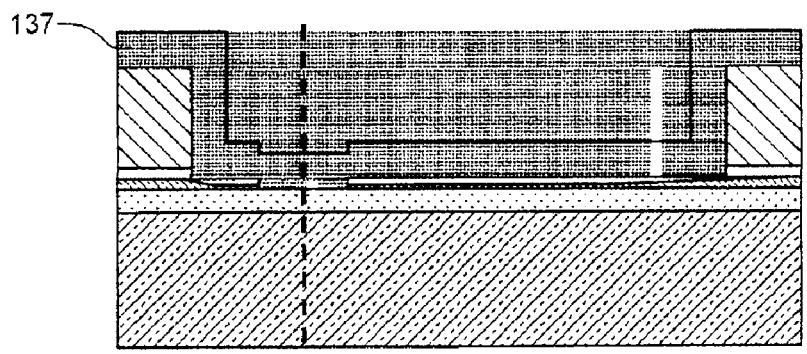
Figure 1E:
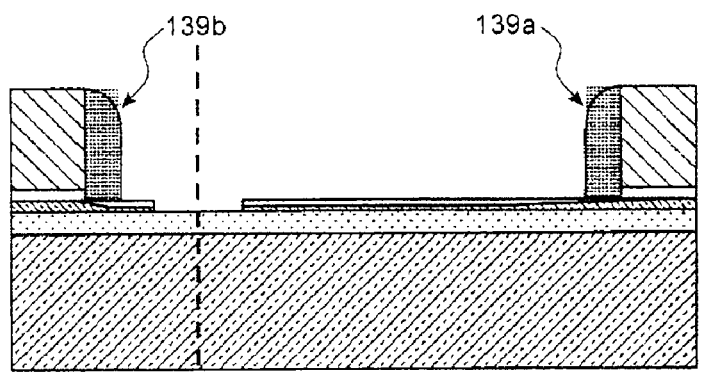
Figure 1F:
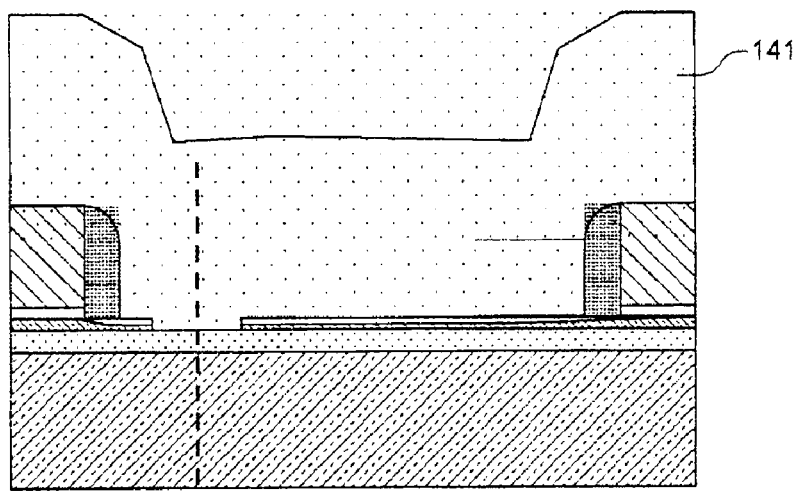

Thereafter (FIG. 1D), a layer of dielectric material 137 is deposited, e.g. $Si_3N_4$, which is etched to maintain insulating regions against the sidewalls of the gates 135, 136, these insulating regions forming spacers 139a, 139b for the first-type transistors and second-type transistors respectively (FIG. 1E).

The gates 135 of the first-type transistors are intended to be a least partly removed, to form special transistors dedicated to the detection of biological elements.

Figure 1G:
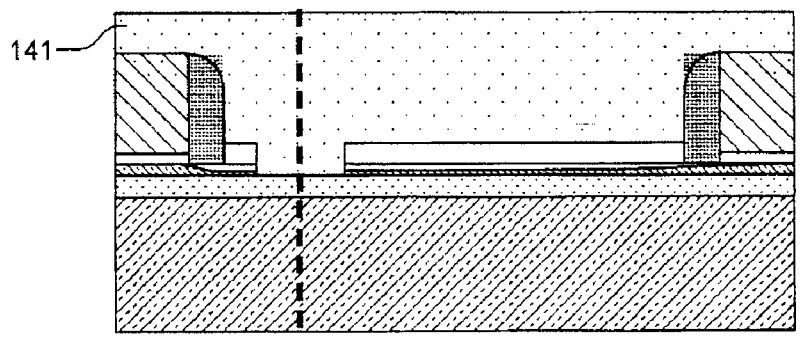

A layer of insulating material 141, in $SiO_2$ for example, whose thickness may be greater than the thickness of the dielectric layer 132, is then deposited so as to coat all the transistors. The deposit of insulating material 141 may be a conforming deposit. Polishing of the layer of insulating material 141 can then be conducted, for example using Chemical Mechanical Polishing—CMP (FIG. 1G).

One or more holes 143 are subsequently formed in the insulating layer 141, to expose the gates 135 of the first-type transistors, provided for the detection of biological elements.

According to one possibility, several holes 143, each exposing at least one gate 135 of a first-type transistor, can be formed.

According to another possibility, only one hole 143 can be formed, exposing several gates of the set of gates 135 of the first-type transistors.

The hole 143 or holes 143 made may be given dimensions and in particular an expanse that is greater than that of the surface of the upper face of the gates 135 of the first-type transistors, so as to expose the entirety of the upper face of these gates 135.

This may allow possible misalignment problems to be overcome with respect to the gate patterns.

Figure 1H:
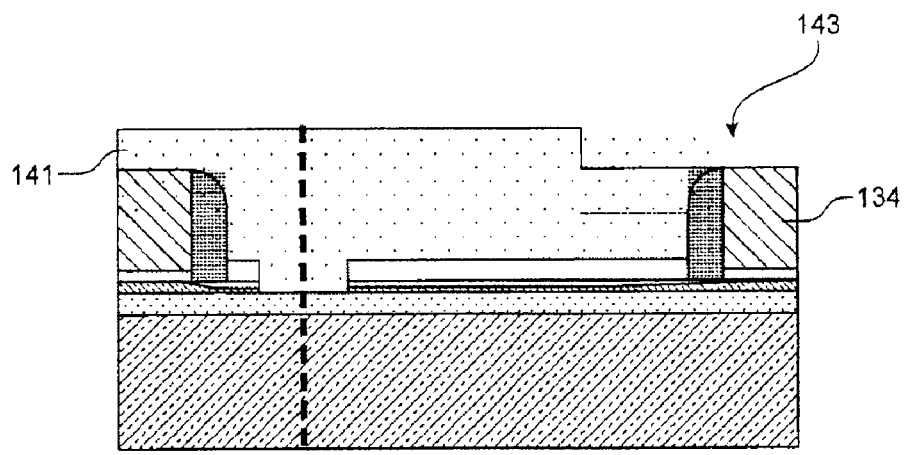
Figure 1I:
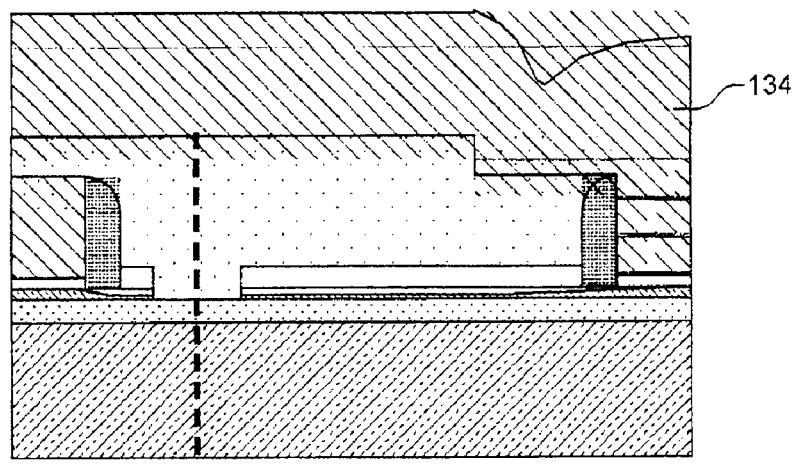

The hole 143 (or holes 143) may, for example, be formed by photolithography followed by etching of the insulating layer 141 (FIG. 1H).

The hole 143 or holes 143 are then filled with a given material 144 chosen so that it can be etched selectively with respect to the material of the insulating layer 141.

The given material 144 may be the same material as the one used to form the gate electrodes 135, 136. In this case, this may allow the subsequent removal of the given material and of the gates 135 to be made at the same time, or during the same etching step, and facilitate subsequent removal of the gates 135 of the first-type transistors.

The given material 144 may be polysilicon for example. Blocks 145 in material 144 are thus formed over the gates 135 of the first-type transistors.

The material 144 may have been deposited so as to flow over the mouth of the holes 143. In this case, a polishing step e.g. using CMP may be conducted to remove excess material 144 lying in a region located above the upper face of the insulating layer 141. Blocks 145 in material 144 are maintained over the gates 135 of the first-type transistors.

Figure 1J:
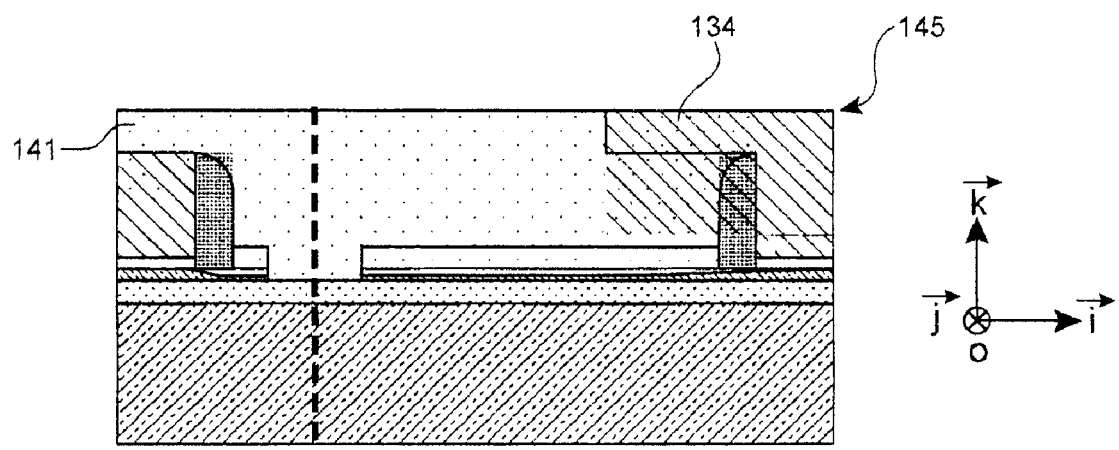

These blocks 145 may have a critical dimension greater than that of the gates 135 on which they rest, and in particular may have a surface, measured in a plane parallel to the plane parallel to the main plane of the substrate (the main plane of the substrate 100 being defined as a plane passing through this substrate and parallel to plane [o; $\vec{i}$; $\vec{j}$] of the orthogonal reference [o; $\vec{i}$; $\vec{j}$; $\vec{k}$] in FIG. 1J) which is greater than the surface of the gates 135 measured along the same plane (FIG. 1J).

Figure 1K:
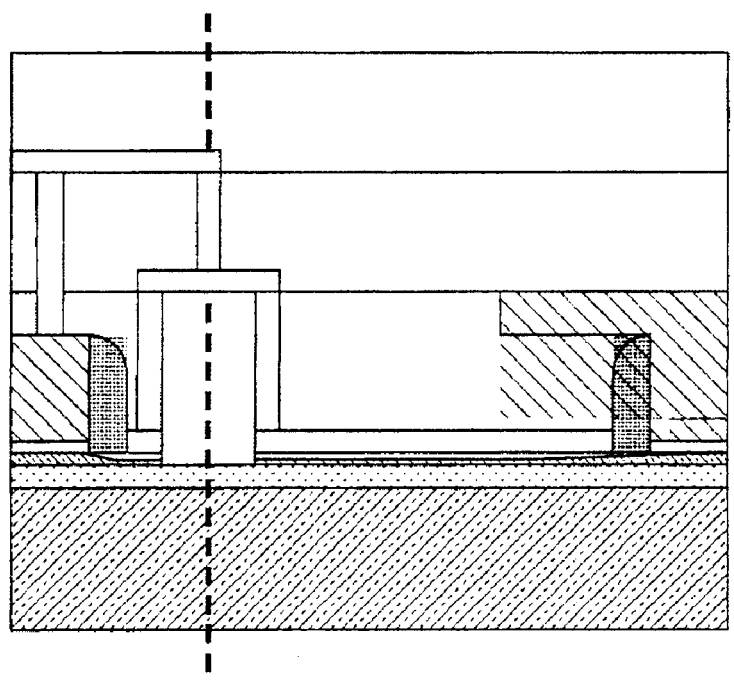

Next, one or more superimposed interconnection levels $N_1, \ldots, N_m$ are formed, in particular for the second-type transistors. Each interconnection level is formed in at least one insulating layer e.g. in $SiO_2$, and comprises one or more vertical conductive elements 147 (i.e. orthogonal to the main plane of the substrate) passing through this insulating layer. The vertical conductive elements 147 may, for example, be in W and are commonly called "vias" 147. Each interconnection level is also formed of one or more horizontal conductive lines 149 (i.e. parallel to the main plane of the substrate) e.g. in AlCu (FIG. 1K).

Next, opposite the first-type transistors, an opening 153 or several openings 153 are formed in the insulating layers $C_1, \ldots, C_m$ in which the different interconnection levels $N_1, \ldots, N_m$ are made, opposite the first-type transistors, so as to expose the blocks 145 in material 134, formed above the first-type transistors.

The opening 153 (or openings 153) may optionally be made by means of a method comprising at least one photolithography step using an identical mask to the mask used to form opening 143 or openings 143 in the insulating layer 141.

Figure 1L:
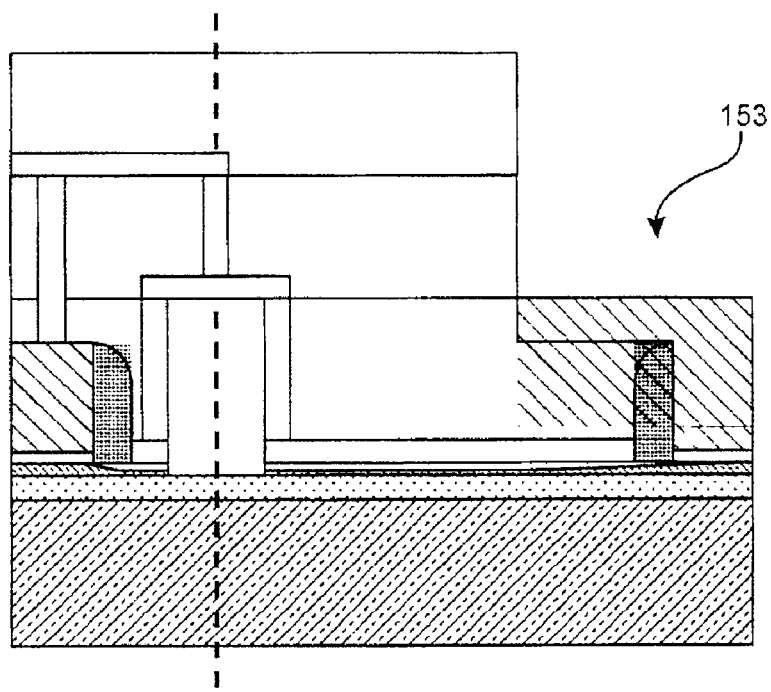

The opening 153 or openings 153 may be of identical shape to the opening(s) 143 previously made in the insulating layer 141 (FIG. 1L).

Figure 1M:
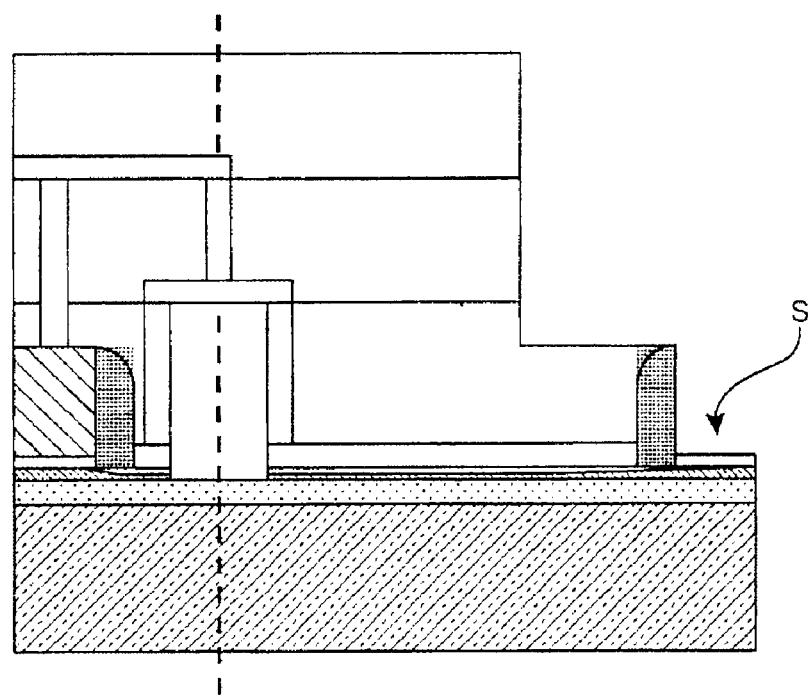

Next, the blocks 145 in material 134 and at least part of the gate patterns 135 of the first-type transistors in gate material 134 are removed, for example by etching the gate material 134. This etching can be conducted using Tetra Methyl Ammonium Hydroxide—TMAH (FIG. 1M).

According to one first possible implementation (not shown), a narrow thickness of gate material may optionally be maintained. The maintained thickness of gate material may, for example, lie between 5 nanometers and 300 nanometers, e.g. at least narrower than the thickness of the first layer 134.

According to a second possible implementation (FIG. 1M), the etching may be performed so as to expose the gate dielectric regions 132 of the first-type transistors. The dielectric 132 may also be at least partly removed, for example using HF etching.

The dielectric 132 may optionally be partly etched, so as only to maintain a thickness of between a few Angströms and 10 nanometers for example.

According to one variant, the total dielectric thickness 132 may subsequently be removed; for example using HF etching so as to expose the active regions 104a.

The surface S is then chemically functionalized with a binding layer 155 on which biological receptors Mr will then be bonded or grafted. The biological receptors Mr may be bonded or grafted via a set of binding linkers themselves bonded to the surface S.

The grafting or binding of biological receptors may be preceded by a step to clean the surface S between the spacers 136a of the first-type transistors and opposite the channel region, for example using an acetone/ethanol rinse. Activation of this surface S can then be performed to give rise to the formation of oxygen functional groups e.g. hydrophilic groups. This activation can be performed using a wet process of Brown type for example or of Caro type, using a dry plasma for example such as an $O_2$ plasma.

Chemical functionalization of the surface S allows a binding layer 155 to be created or binding linkers intended to receive the biological receptors Mr.

The binding layer 155 may have a thickness of between 1 nm and several tens of nanometers. The binding layer 155 (or binding linkers) may be of organic type.

According to one possibility, the layer 155 may be designed to be nucleophilic, whilst the biological receptors Mr bonded to this layer are electrophilic.

In this case, the binding layer 155 may comprise one or more nucleophilic functions or groups such as one or more amine, oxyamine, alcohol, thiol functions or groups.

According to another example, the binding layer 155 may be designed to be electrophilic, whilst the biological receptors Mr bonded to this layer are of nucleophilic type.

The region that is more particularly functionalized is the region located facing the channel region of the first-type transistors, and which may be in a gate dielectric if a thickness of gate dielectric 132 has been maintained, or optionally in gate material 134 if a thickness of gate material 134 has also been maintained.

A biological receptor Mr is a biological molecule bonded to the surface S via a binding layer 155 or binding linkers, and having a specific affinity for a biological element to be detected, also called a "biological marker".

The biological receptors may be designed to receive at least one biological marker such as at least one protein for example, or an antibody (e.g. of PSA, TSH type) or at least one virus (e.g. influenza) or may comprise nucleotides and be designed to receive DNA.

The biological receptors may, for example, be oligonucleotides (15-80 bases), or PCR elements i.e. DNA strands of several hundred to several tens of thousands of base pairs for example, or proteins, or antibodies for the detection of antigens, or fragments of antibodies comprising at least one site allowing biological affinity.

The functionalisation of receptors can be performed by binding or grafting biological receptors on an organic layer or on organic linkers formed on said surface S, in a region located opposite or above or on active regions 104a of the first-type transistors, in particular in a region lying opposite or above or on a region of the first-type transistors intended to act as transistor channel region.

Figure 1N:
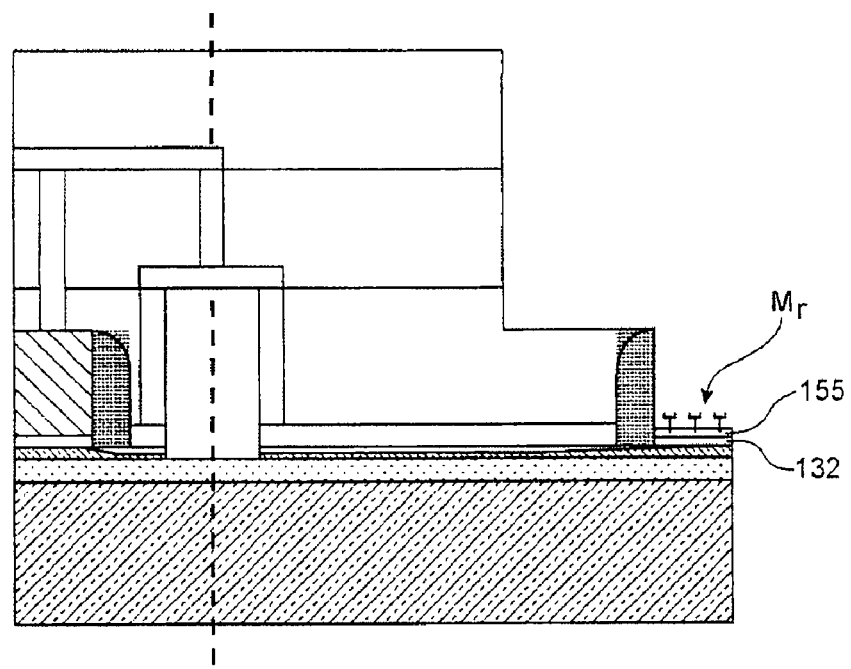
Figure 1O:
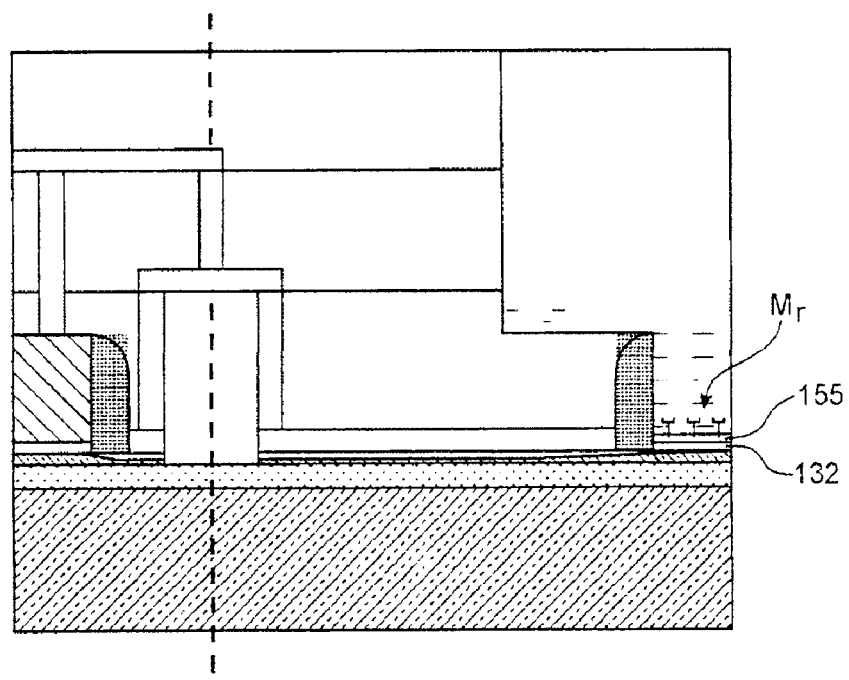

In FIG. 1N, the functionalisation of the surface S with a binding layer 155 on which biological receptors Mr are bonded or grafted, is made on the dielectric region 132.

Figure 2A:
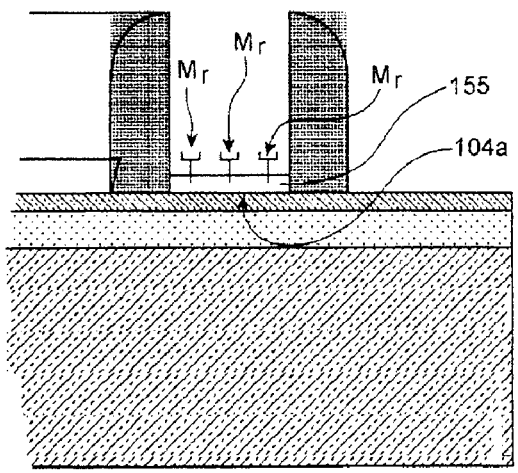
FIGS. 2A-2C illustrate examples of transistors formed using a method according to the invention and dedicated to the detection of biological elements, the transistors in FIG. 2A comprising identical receptor molecules attached opposite a channel region, and the transistors in FIG. 2B comprising several different receptor molecules attached opposite a channel region, and the transistors in FIG. 2C comprising receptor molecules in an encapsulating layer.

According to another possibility (FIG. 2A), the functionalisation of the surface S with a binding layer 155 on which biological receptors are bonded or grafted, may optionally be performed directly on the surface of the channel regions of the first-type transistors, if the gate dielectric 132 and the gate material 134 have been fully removed between the spacers 139a of the first-type transistors (FIG. 2A).

The biological receptors, also called biological probes, can therefore be immobilized on channel semiconductor regions, or optionally on regions of gate dielectric material.

The functioning of the semiconductor components for detection of biological elements, formed by means of said method, rely on variation in electric conductivity of a semiconductor channel, in relation to the presence and quantity of biological elements intended to be placed on receptor molecules formed on or opposite the channel semiconductor region.

According to one particular embodiment, the biological receptors Mr can be designed or used to receive DNA. In this case, the biological receptors Mr may comprise oligonucleotides, PCR products, or DNA fragments.

The biological probes Mr may lie on the surface S, in the form of a layer which may have a thickness of several Angströms for example, or a thickness of between several Angströms and around one hundred nanometers.

The layer of biological probes Mr may optionally have a thickness of between 1 nm and 10 nm for example, and be formed of several sub-layers of biological receptors.

The biological probes or receptor molecules may be bound to the surface S covalently or they may be adsorbed. Binding said molecules via one or more covalent bonds may allow improved robustness to be obtained.

As indicated previously, the receptor molecules Mr may be bonded to the surface S via at least one specific chemical linker, which allows facilitated binding of the biological probe and/or adaptation of the properties of the organic/inorganic interface, such as rigidity, electric conduction, between the organic linkers and the receiving region of the biological probes. If the specific chemical linkers are intended to bind the biological probes, these linkers comprise a chemical function capable of reacting with the biological probes, so as to set up a covalent bond, or an electrostatic interaction for example an interaction of hydrophobic type or Van der Waals type. As an example, the covalent bond between the "linker" and the "biological probe" may, for example, be formed of a bond of one or other of the following types: C—N, C=N (imine), C—O, amide, ester, triazole e.g. from a reaction between an alkyne and an azide group.

The biological probe Mr and its linker comprise a chemical group adapted to enable the probe to bind to the surface S.

If the surface S is in a dielectric material such as $SiO_2$, $Si_3N_4$, $TiO_2$, the biological probes Mr or linkers used may be provided with silane functions for example such as: —$SiH_3$, R—SiX3, R2SiX2, R3SiX, in which R is a carbon group and X is a releasable group of halogen or alcoxy type, or phosphates or phosphonates.

If the surface S on which binding is made is in a semiconductor material such as silicon, the functions which may be used may comprise Si—C or Si—O bonds, for example using alkene, alkyne, alcoxy, phenol, diazonium and halide functions, in order to bind the receptors Mr.

Depending on the type of receptor layer it is desired to produce, i.e. a single layer or several layers, a thin layer in the order of a nanometer for example and a thick layer in the order of around one hundred nanometers, the binding of the biological probes can be carried out differently.

If it is desired to form a single layer and/or a thin layer, this can be produced for example by dipping the surface S in a solvent containing the molecules to be bonded: i.e. biological probes Mr and/or linkers optionally in the presence of one or more catalysts.

A so-called "Langmuir Blodgett" method can also be used, such as described for example in the document by I. R. Peterson, "Langmuir Blodgett Films", J. Phys. D 23, 4, (1990) 379-95.

Figure 3:
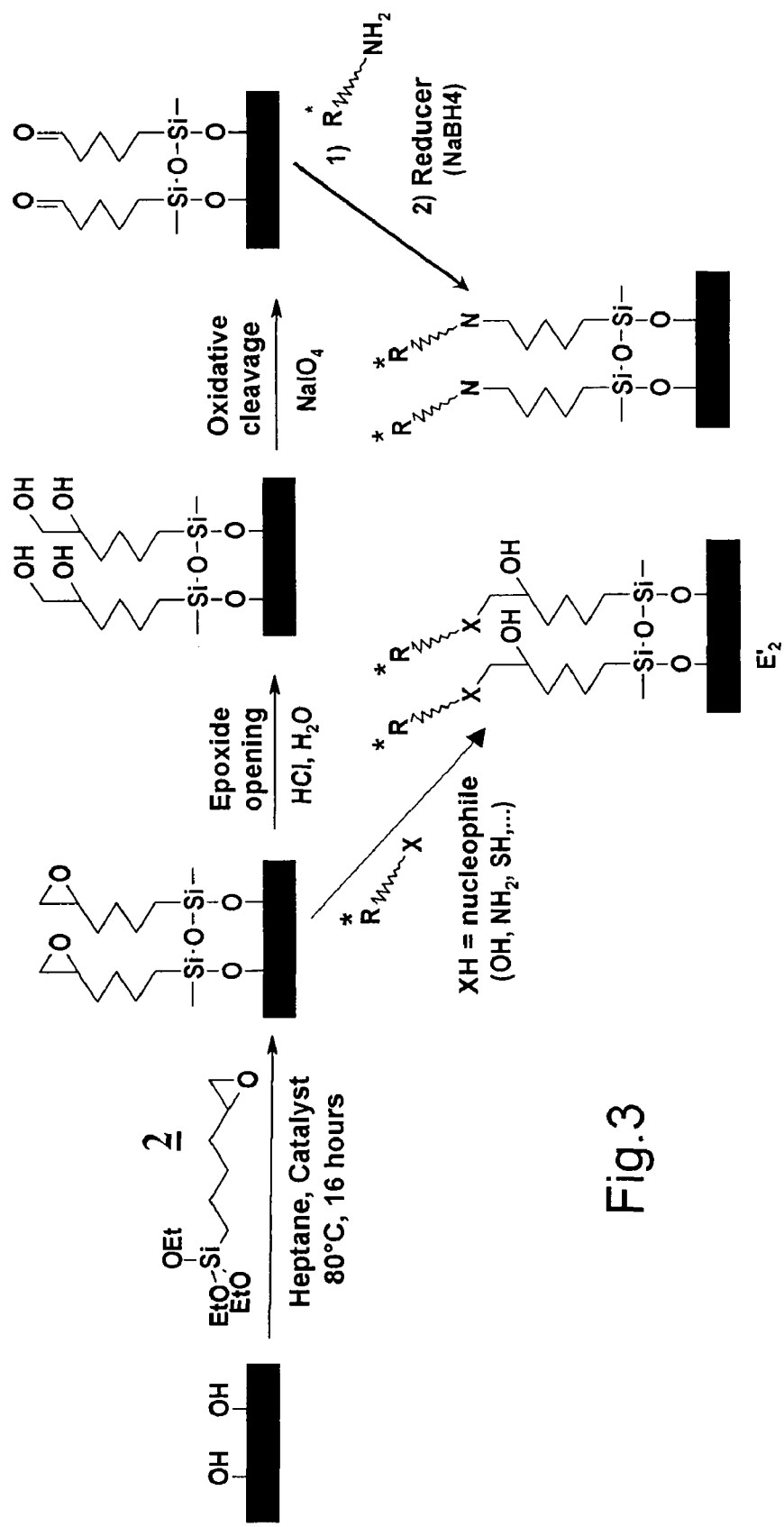
FIG. 3 illustrates a particular example of a method to bind or graft receptor molecules containing at least one nucleophilic function, on a region located opposite a channel of a transistor intended for the detection of biological elements.

A first particular example of the method to bind receptors comprising a nucleophilic function is given in connection with FIG. 3.

To achieve binding of the receptors comprising a nucleophilic function, firstly the surface on which grafting is to be performed must be activated.

Silanisation in an anhydrous solvent for example, such as toluene, can then lead to obtaining epoxide functions. This silanisation allows epoxide type functions to be obtained on the surface that are reactive with receptor molecules containing nucleophilic functions.

The receptor molecules are then immobilized and bonded irreversibly. This irreversible immobilization may be performed by creating a covalent bond obtained by opening an epoxide cycle with the nucleophilic function in an acid, basic or neutral medium.

It is also possible to convert the epoxide function into a diol then an aldehyde function, and then to bond the biological molecule thereto.

This second route comprises more steps but allows the surfaces to be maintained in a stable state (diol) before use.

According to a second particular example of the binding method, in which the receptor molecules Mr are intended to receive DNA strands for example:

First, the surface S is chemically prepared so as to obtain epoxide functions, followed by immobilization of the receptor probes, which in this example are in the form of nucleic acid fragments.

The epoxide functions may be formed by deposit e.g. using a robot provided with piezoelectric heads. The probes can then be hybridized with a complementary target.

An oligonucleotide modified by a $NH_2$ function for example can be deposited at a concentration in the order of 10 tM for example in an aqueous saline solution such as $Na_2HPO_4$ at 0.3 M, using a robot provided with piezoelectric heads. The volume of drops deposited may be in the order of several hundred picoliters for example.

After a reaction time of around 15 hours for example, washing is carried out to remove the excess probes which have not reacted with the surface on which their binding is desired. This washing may be performed in water for example and a 0.3 M base solution of $Na_2HPO_4$ and/or a reducing solution containing $NaBH_4$ for example at a concentration in the order of 0.1 M.

The receptor probes are then hybridized by a complementary target e.g. of 20 mers at a concentration possibly varying from around several fM to several μM.

The transistors formed using said method can be used to carry out the detection of charged target DNA strands, by measuring the conductance or variation in conductance of the channel region subjected to a change in its electrostatic environment, subsequent to receiving of DNA strands by the grafted targets.

To come back to the fabrication of the microelectronic device such as described above in connection with FIGS. 1A-1N, the biological probes Mr may also be deposited using the technique known as "spotting".

Figure 2B:
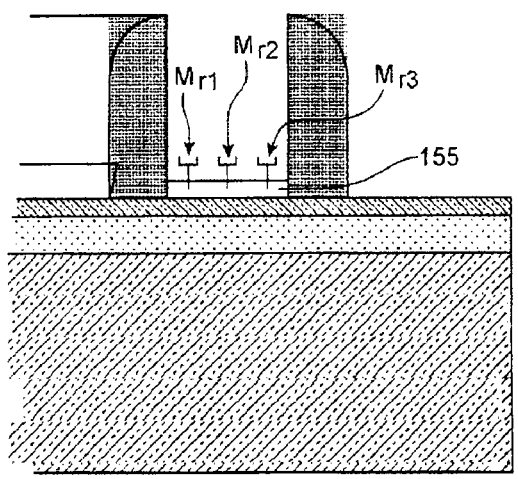

According to one possible implementation, different probes i.e. different molecules of biological receptors $M_{r1}$, $M_{r2}$, $M_{r3}$ may be bonded opposite one same channel region (FIG. 2B). Using a "spotting" method, it is possible for example, on one same substrate, to deposit different probes Mr1, Mr2, Mr3 at different points.

Figure 2C:
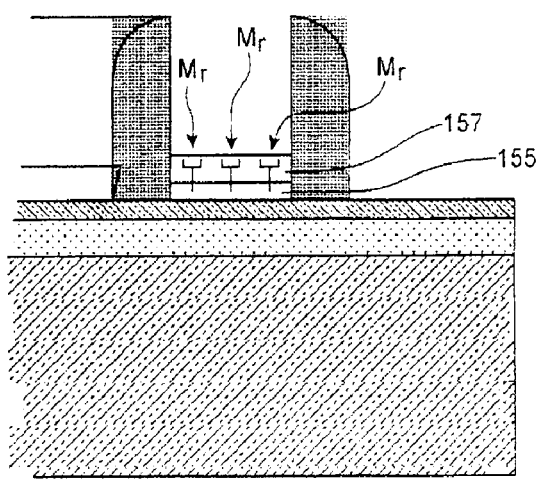

The biological receptors Mr may be left free or, according to another possibility (FIG. 2C), they may be encapsulated or coated in a layer 157 called a "matrix" layer which may be in a material of solgel or polymer type, and having a thickness of between several nanometers and several hundred nanometers. Depending on its formulation, this material may be porous allowing the entry of some fluids.

A thick encapsulating matrix 157, in a polymer for example, can be formed using a solgel process comprising dipping and withdrawal steps, or spin-coating or laminar coating or spraying. Said encapsulation in a matrix 157 can allow transistors to be used having a greater molecular surface density. Without a matrix, a density of the order of 1,000 molecules/$\mu m^2$ for example can be obtained. With encapsulation, a density of the order of 100,000 molecules/$\mu m^2$ for example can be obtained, thereby increasing the sensitivity and/or robustness of the detection system.

Once the receptor molecules Mr have been functionalized, a fluid in particular a liquid can be added e.g. a buffer solution, through the openings 153. Said liquid is intended to receive or contain biological elements to be analyzed, which can be received by the biological receptors (FIG. 1O).

An enclosure can be formed around the detection circuit, for example by forming a cover over the detection circuit.

A sealed enclosure may be set up so that it is possible in particular to enclose a fluid e.g. the biological buffer liquid.

Sealing may be achieved by serigraphy using an adhesive e.g. an UV-activated adhesive. Said method of sealing dispenses with a high temperature method which might deteriorate the receptor molecules Mr of the biological elements.

Glass capillaries having an inner diameter of the order of 100 μm for example, may be provided in the device to allow circulation of a biological fluid intended to convey biological markers and to be positioned on regions S of the first-type transistors comprising receptor molecules Mr.

The method just described allows implementation of a device comprising, on one same substrate, both special transistors dedicated to biological detection as well as transistors provided with a gate of which some may be designed for the processing of signals acquired by the transistors detecting biological elements, on this one same substrate. The special transistors dedicated to the detection of biological elements are components provided with a semiconductor channel and with receptor molecules bonded to a surface lying opposite the channel, the conductivity of the channel varying in relation to the biological elements present on the receptor molecules.

Figure 4:
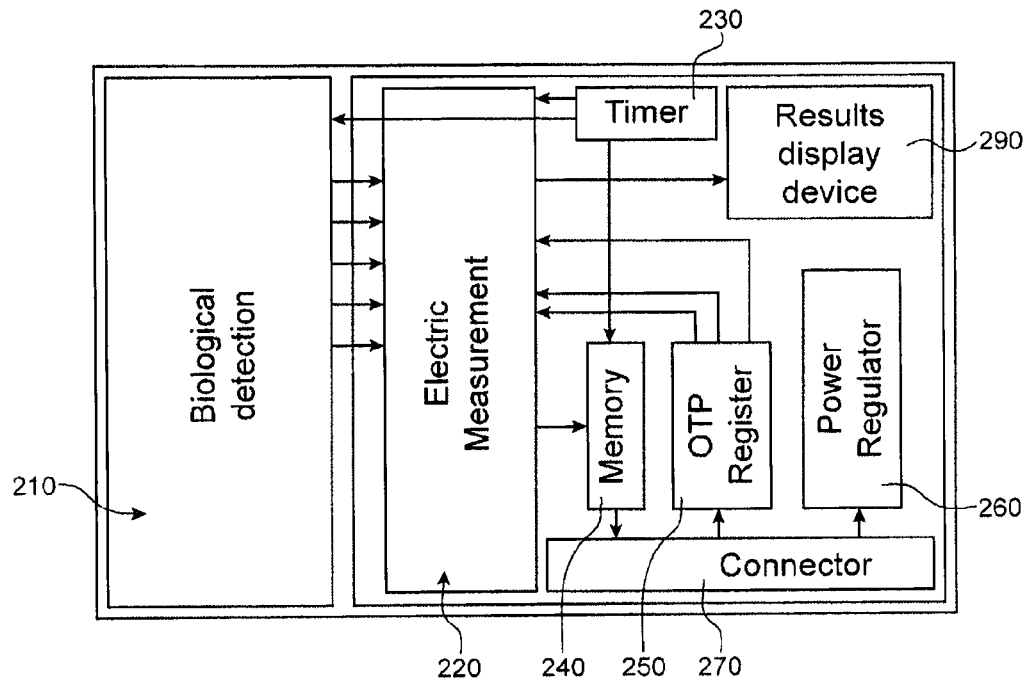
FIG. 4 illustrates an example of chip for the detection of biological elements, comprising at least one detection circuit to detect biological elements and at least one processing circuit to process signals detected by the detection circuit of biological elements, FIG. 5 gives examples of curves representing quantities of markers used for the detection of HIV, as a function of time.

A method such as previously described allows the use of a microelectronic device, in particular a chip intended to conduct diagnosis or pre-diagnosis or part of a medical diagnosis. One example of a chip for the detection of biological elements, fabricated using a microelectronic method of the type just described with reference to FIGS. 1A-1N, is given FIG. 4.

The chip comprises a circuit or biological detection module 200 comprising transistors for the detection of biological elements and in particular of biological markers (such as those described previously in connection with FIGS. 1A-1N). This detection module is intended to supply electric measurement signals to a circuit 220 or to a module 220 for processing of the electric signals delivered by the detection circuit. This circuit may be designed to conduct reading of detected signals, to convert measurements into digital data, the measured digital data then being processed. Processing such as amplification, comparison, analog-digital conversion filtering, may in particular be conducted. The module 220 may be designed to detect a variation in conductance of the biological detection transistors, this variation in conductance being amplified then compared with a threshold, determined by means of an OTP register, via a comparator which is able to deliver a binary digital signal.

This information may be used to conduct part of a diagnosis and to determine whether or not a concentration of molecule X exceeds a predetermined threshold after a predetermined time fixed by programming a sequencer module 230 known as a "TIMER". This timer 230 is provided to give a time base, in particular to the biological detection module 210, to module 220 and to at least one memory 240.

The timer 230 is intended to manage sequencing of detections, restitution of measurements and their memorization. Said sequencing is adapted in relation to the application and to the type of diagnosis to be carried out.

A data memory 240 can be provided to store measurement data derived from module 220.

A programme memory module 250 or programmable register 250 e.g. of One Time Programmable type—OTP, is also provided. Said module may notably include recorded reference values or recorded ranges of reference values. Recorded reference values may for example be quantity thresholds of biological elements such as biological markers to be detected.

Each block of the chip can be placed in service or deactivated via the timer 230 which is programmed via module 250 to adapt the time base of measurements or sequencing of measurements to the diagnosis to be made. Once the time needed for a diagnosis or a first measurement or a first series of measurements has lapsed, the timer 230 can set in operation the measurement processing module 220 and trigger memorization of measured, processed data in the memory 240.

A power regulator 260 can be provided to allow a first voltage e.g. of the order of 2.5 volts or possibly reaching 3.3 volts, delivered by a battery for example to be converted to a second voltage adapted to the technology of the different modules 210, 220, 230, 240, for example a voltage of the order of 1.8 volt. It is also possible to use an external voltage source commonly called a bench-top supply or stabilized supply.

Connectors 270 may be provided between the power regulator 260 and one or more other modules, for example the regulator and the memories 240, 250.

Connectors 270 may be provided to interface the circuit with the outside, for example to read the content of the memory 240, or to programme the OTP register 250 or to power the circuit.

A display device 290 may also be provided on the chip.

Measurements of the presence of one or more biological markers after predetermined durations or periods T may be conducted.

According to one particular application, said chip may be dedicated to and used for conducting diagnosis or pre-diagnosis or part of a medical diagnosis.

A series of different tests or automated operations can be implemented by the chip to determine a diagnosis or pre-diagnosis.

Amongst these operations the chip is adapted to implement:

memorization of data on measurements made said by detection circuit, comparisons of measurements made with reference values, or with ranges of reference values memorized in the register 240.

The chip can also be used to detect differences between measurements made by the detection circuit and reference values.

Several examples of operations or tests, which can be carried out by a chip for the detection of biological elements according to the invention, will now be described.

A test called an "alert test" comprising a logic operation of OR type, can be implemented for example to detect the onset of at least one 1st biological marker in time.

The chip may be used to determine one or more profiles, each representing a quantity of at least one given biological marker detected over time. Said profiles may be in the form of a set of discrete data on the detected quantity of biological markers or elements collected over time.

The chip may also be used to determine at least one comparison of these profiles with standard or reference profiles, for example.

A test of "yes/no" type can then be implemented to indicate whether, subsequent to a comparison between one or more measured profiles, this or these measured profiles correspond to or are close to a standard or reference profile.

Another type of test called a "semi-quantitative" test, used to associate data derived from measurements made, with a level indicator for example a disease risk level indicator from among several predetermined levels, can also be carried out.

The chip can therefore also be used to determine one or more comparisons of a quantity of biological elements such as biological markers, with ranges of reference values, and in relation to this comparison to deliver a level indicator e.g. a level indicator of risk of disease.

A semi-quantitative test can be conducted for example, provided to deliver a risk level from among 3 different risk levels: "low", "moderate", "high" corresponding to 3 ranges of quantity values of different markers.

One example of an algorithm for a semi-quantitative test may be the following:

If marker_1=high OR marker_3=high, then risk_level_1=5.

If marker_1=high OR marker_2=high, then risk_level_2=high.

If risk_level_1+risk_level_2>THRESHOLD, then diagnosis is positive.

Ranges of values may be useful to determine a first diagnosis or pre-diagnosis.

Examples of applications of the chip described above for the diagnosis of different diseases or pathologies will now be given.

A first example of application concerns myocardial infarction.

Examples of the kinetics of the onset of different markers used for the detection of this pathology are listed in Table I below.

TABLE I

| Marker | MW (kDa) | Time of onset | Peak | Normalisation* |
|---|---|---|---|---|
| Myoglobin | 17 | 2-3 h | 8-12 h | 24-36 h |
| LDH | 134 | 12-16 h | 30-40 h | 8-12 days |
| CK | 86 | 6-8 h | 20-26 h | 3 days |
| CK-MB mass | 86 | 3-8 h | 10-24 h | 3-4 days |
| CK isoforms | 86 | 1-4 h | 4-8 h | 1-2 days |
| Cardiac troponine T | 19.8 | 3-12 h | 12-48 h | 5-14 days |
| Cardiac troponin I | 24 | 6-12 h | 2-4 days | 6-10 days |
| Myosin light chains | 18 | 6-12 h | 2-4 days | 6-12 days |
| Myosin heavy chains | 215 | 24-36 h | 5-6 days | 14 days |

*if no complications or thrombolytic therapy.

It is possible, for example, to associate detection of early markers such as Myoglobin (2-3 h) with detection of definitive markers such as CK-MB or troponins T and I, to confirm a diagnosis of the risk of onset of this pathology.

It is also possible to consider a test allowing monitoring of myoglobin, and if there is an increase in the myoglobin level beyond a predetermined threshold, to move on automatically to the monitoring of other markers. This makes it possible not to monitor all the markers at the same time, and for example allows a reduction in data flow or chip consumption.

In Table II below, examples of markers are given which can be used to determine early, definitive or delayed diagnosis, and of biological markers for determination of the size of a necrosis or success of reperfusion.

TABLE II

| Situation | | Useful markers |
|---|---|---|
| Diagnosis | Early | MGB, CK-MBm, CK isoforms |
| | Definitive | cTnI, cTnT |
| | Delayed | cTnI, cTnT |
| Size of necrosis | | MGB |
| Success of reperfusion | | MGB, cTnT, CK isoforms |

A second example of application concerns the process of HIV detection (human immunodeficiency virus). For this application, detection of 3 types of different markers can be used.

Figure 5:
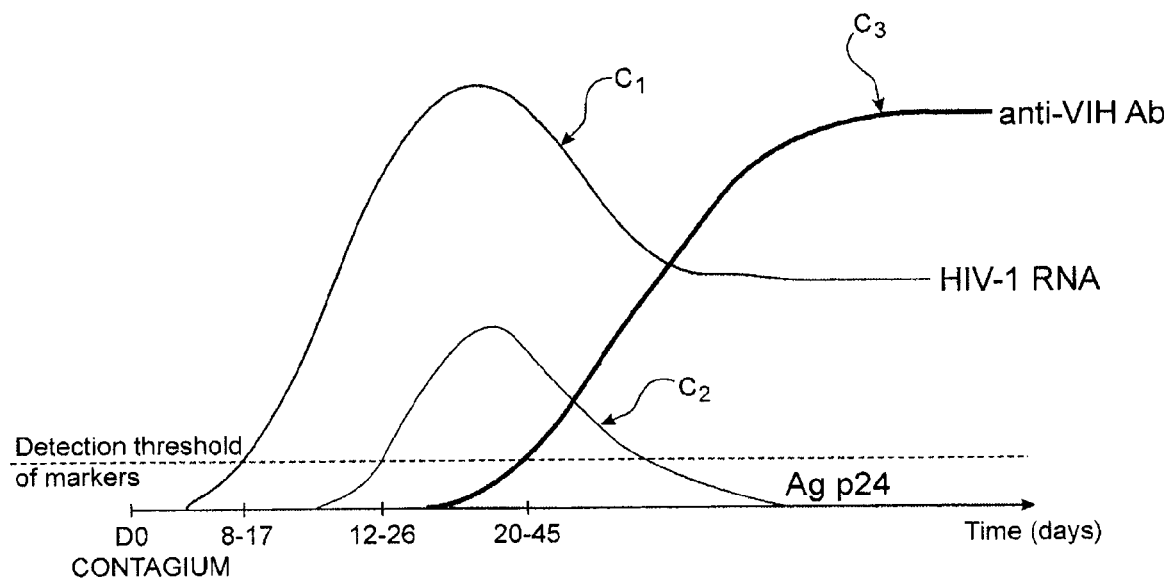

In FIG. 5, examples of curves are given representing the quantities of markers used for HIV detection, as a function of time.

A first early marker is HIV-1 RNA (curve C1 in FIG. 5).

Monitoring of the HIV-1 RNA level can be carried out. When this level increases significantly and exceeds a predetermined threshold, the monitoring of a second marker can be trigged: AgP24 (curve C2), and optionally a third marker: Ac anti-HIV1 (curve C3).

A third application is the detection of cancer markers.

Elevation of a marker to "moderate" may be due to a benign cause rather than to the effective presence of a cancer.

Elevation of several markers to "substantial" may however be significant.

Alert thresholds for quantities of markers may be determined, and depending on the quantities of detected markers, these quantities can be associated with a cancer risk level.

Different cancer pathologies and their respective markers are given as examples in Table III below:

TABLE III

| | | Mucinous tumours | CA19-9, ACE |
|---|---|---|---|
| PROSTATE | | ADK | PSA, FPSA |
| TESTICLE | | Seminoma | HCG, AFP |
| | | Nonseminoma | HCG, AFP |
| COLORECTAL | | ADK | ACE, CA 19-9, CA 125 |
| PANCREAS | | ADK | CA 19-9, ACE |
| | | Endocrine | CA 19-9, ACE, NSE |
| LIVER | | Hepatocarcinoma | AFP, ACE |
| STOMACH | | ADK | CA 72-4, CA 19-9, ACE |
| ESOPHAGUS | | ADK | ACE |
| | | Epidermoid | SCC, CYFRA 21-1 |
| THYROID | | Medullary | ACE, NSE |
| | | Differentiated | Thyroglobuline |
| LUNG | | ADK | ACE, CA 19-9, CA125 |
| | | Epidermoid | CYFRA 21-1 |
| | | Small cell | NSE, CA 125 |
| BLADDER | | | TPA, SCC, ACE, CYFRA |

Table IV below indicates increases which can be qualified as "strong" or "moderate" in relation to the markers present in the preceding table.

TABLE IV

| Markers | Units | Normal | Moderate increases | Strong increases |
|---|---|---|---|---|
| ACE | ng/ml | <5 | 5-10 | 10-100,000 |
| AFP | ng/ml | <15 | 15-200 | 200-10,000 |
| PSA | ng/ml | <4 | 4-10 | 10-1,000 |
| CA 15-3 | U/ml | <40 | 40-60 | 60-30,000 |
| CA 19-9 | U/ml | <35 | 35-100 | 100-1,000,000 |
| CA 125 | U/ml | <35 | 35-50 | 50-50,000 |
| CA 72-4 | U/ml | <6.9 | 7-30 | 30-10,000 |
| BHCG | mUI/ml | <5 | >5 | 5-100,000 |
| B2M | mg/ml | <2 | >2 | 2-10 |
| NSE | ng/ml | <21 | 21-50 | 50-4,000 |

The invention claimed is:

1. A method to fabricate a microelectronic device provided with at least one circuit to detect biological elements, comprising the steps of:
   a) forming, on a substrate, a plurality of transistors each comprising at least one gate formed of at least one layer in at least one gate material on at least one layer of gate dielectric, said gate resting on a channel region,
      depositing at least one layer in at least one insulating material coating said transistors,
      forming one or more holes in said layer of insulating material, so as to expose the upper face of the respective gate of the so-called "first-type" transistors among said transistors, whilst one or more other so-called "second-type" transistors among said transistors are coated with insulating material,
      filling the holes with gate material chosen so that it can be etched selectively with respect to the insulating material, the filling allowing the formation of blocks in said gate material respectively resting on the upper face of the gates of the first-type transistors,
   b) removing said blocks in said gate material, and removing at least in part the respective gate of the first-type transistors, whilst the respective gate of one or more other transistors called "second-type transistors", amongst said transistors, is protected,
   c) binding biological receptors on a surface located facing the channel region of the first-type transistors, these receptors intended to receive one or more biological markers.

2. The method according to claim 1, wherein said holes have a bottom part whose surface is greater than the surface of the upper face of the gate of said first-type transistors.

3. The method according to claim 1 wherein, after filling said holes with said given material, one or more insulating layers are formed and one or more interconnection metal levels facing said second-type transistors and wherein, the method further comprises the forming, opposite the first-type transistors, of one or more openings in said insulating layers so as to expose the blocks in said given material, the removal of the given material and the removal of the gate material at step b) being made through said openings.

4. The method according to claim 1, wherein the biological receptors are bonded via binding linkers or a binding layer in particular of organic type.

5. The method according to claim 1, wherein the biological receptors are bonded via binding linkers or a binding layer formed on the channel region of the first-type transistors or on said gate dielectric layer of the first-type transistors.

6. The method according to claim 1, wherein the biological receptors are inserted in an encapsulation layer.

7. The method according to claim 1, wherein the biological receptors are designed to receive at least one biological marker, such as at least one protein, or at least one virus, or at least one antigen, or they contain nucleotides and are intended to receive DNA.

8. The method according to claim 1, further comprising after step c), filling of said openings with at least one liquid intended to act as conveyor of biological elements to be detected.

* * * * *